(12) United States Patent
Freeberg

(10) Patent No.: US 6,904,311 B2
(45) Date of Patent: Jun. 7, 2005

(54) METHOD OF DETERMINING AND DOCUMENTING CESSATION OF LIFE USING EVOKED RESPONSE

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 252 days.

(21) Appl. No.: 10/326,000

(22) Filed: Dec. 19, 2002

(65) Prior Publication Data

US 2004/0122331 A1 Jun. 24, 2004

(51) Int. Cl.$^7$ ............... A61B 5/0402; A61N 1/365; A61N 1/37
(52) U.S. Cl. ............... 600/510; 607/5; 607/9; 607/17; 607/27
(58) Field of Search .............. 600/510, 508–528; 607/17, 27, 4–38

(56) References Cited

U.S. PATENT DOCUMENTS 5,486,200 A * 1/1996 Lindemans ............... 607/5
5,899,866 A * 5/1999 Cyrus et al. ............... 600/510

* cited by examiner

*Primary Examiner*—Jeffrey R. Jastrzab
*Assistant Examiner*—Alyssa M Alter
(74) *Attorney, Agent, or Firm*—Thomas J. Nikolai; Nikolai & Mersereau, P.A.

(57) ABSTRACT

The date and time of death of a patient may be recorded in a memory of a microprocessor used in an implantable cardiac rhythm management device by detecting the failure of the heart to produce an evoked response upon the application of a pace pulse to the heart. To confirm death, other physiologic sensors used in the cardiac rhythm management device may also be sensed to determine the absence of an expected output signal.

8 Claims, 2 Drawing Sheets

METHOD OF DETERMINING AND DOCUMENTING CESSATION OF LIFE USING EVOKED RESPONSE

BACKGROUND OF THE INVENTION

I. Field of the Invention

This invention relates generally to implantable medical devices, and more particularly to a method of precisely defining the moment of death of a patient in whom such a device is implanted.

II. Background of the Invention

Implantable medical devices, such as cardiac pacemakers, pacemaker/defibrillators and other cardiac resynchronizing devices, are frequently used to treat patients suffering from cardiac abnormalities, including arrhythmias, chronotropic incompetence and congestive heart failure. Such patients are often aged or in poor health. By providing properly timed electrical stimulation to the heart, cardiac output can be better linked to metabolic demand, leading to an improved quality of life for the patient.

State-of-the-art cardiac rhythm management devices generally comprise a programmed microprocessor connected in controlling relation to a stimulation pulse generator. At times dictated by a software program executed by the microprocessor, the microprocessor-based controller applies pacing pulses to cardiac tissue via electrodes on electrical pacing leads. The stimulator system will also include one or more sensing circuits for detecting, amplifying and shaping cardiac depolarization signals (electrograms) picked up by the electrodes on the pacing lead. These depolarization signals are applied to the microprocessor-based controller and are used by the software in controlling the times at which stimulating pulses are applied to the heart.

In demand-type pacemakers, pacing is integrated with a patient's own sinus rate and pacing pulses are generated in the absence of an intrinsic heartbeat or in accordance with some other pacing algorithm. Assuming that a pace pulse is of a sufficient amplitude to result in capture of the myocardial tissue, a detectable depolarization signal occurs.

Modern cardiac rhythm management devices include sufficient memory for not only storing programs and programmable parameters used in executing the program, but also to store for later read-out, electrograms covering a predetermined interval of time. By reading out electrogram information using the telemetry capabilities of such devices, a medical professional is able to gain considerable insight into the patient's cardiac performance and the efficacy of a pacing therapy being administered.

When a person dies, it frequently proves helpful to know the exact moment (date and time) when death took place. Also, if a patient in whom a cardiac rhythm management device has been implanted dies, stored electrogram data and other information relating the device's performance may be captured at the time of death, aiding a medical professional in determining how the patient's heart and the cardiac stimulator were functioning up until the moment of death.

It is accordingly a principal purpose of the present invention to provide a method for sensing and recording the time of death of a patient in whom a cardiac rhythm management device has been implanted along with other data.

SUMMARY OF THE INVENTION

The present invention provides a method of sensing the death of a patient in whom a cardiac rhythm management device has been implanted. The cardiac rhythm management device will typically have a ventricular sensing amplifier for detecting natural and evoked cardiac depolarization signals, and a microprocessor-based controller that is coupled to receive an output from the ventricular sensing amplifier and which develop control signals. The control signals are applied to a stimulation pulse generator, causing it to produce cardiac stimulating pulses at timed intervals determined by the control signals. The method includes the steps of monitoring the ventricular sensing amplifier for an evoked response of the patient's heart to the application of the cardiac stimulating pulses and recording in the pacemaker the date and time at which no intrinsic beats are detected by the sensing amplifier and the application of cardiac stimulating pulses cease to produce an evoked response.

In accordance with another aspect of the invention, the microprocessor-based controller will further include a buffer memory for storing electrogram signals occurring during a predetermined time interval and the method for sensing the death of the patient includes a further step of capturing the contents of the buffer memory upon detection that no intrinsic beats are occurring and the application of cardiac stimulating pulses to the heart does not result in an evoked response.

DESCRIPTION OF THE DRAWINGS

The foregoing features, objects and advantages of the invention will become apparent to those skilled in the art from the following detailed description of a preferred embodiment, especially when considered in conjunction with the accompanying drawings.

DESCRIPTION OF THE PREFERRED EMBODIMENTS

Figure 1:
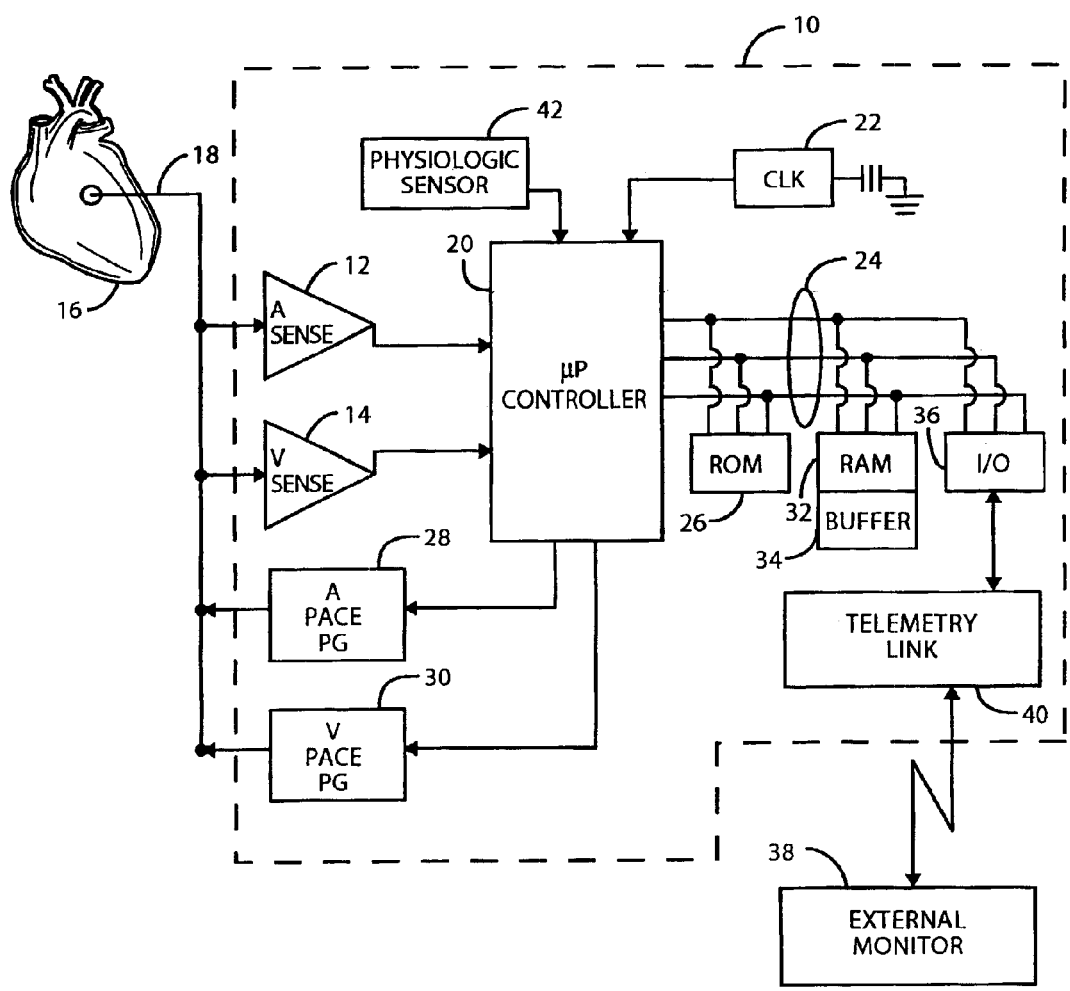
FIG. 1 is a general block diagram of a cardiac rhythm management device in which the method of the present invention is implemented.

Referring to FIG. 1, there is shown enclosed by the broken line box 10 a general block diagram of a conventional cardiac rhythm management device such as an implantable pacemaker or an implantable pacemaker/defibrillator. It is seen to include sensing circuits 12 and 14 for detecting, respectively, atrial depolarization signals (P-waves) and ventricular depolarization signals (R-waves), be they intrinsic beats or evoked responses. If desired, a separate sense amplifier especially tuned to detect evoked responses, may be utilized. The output from the atrial sense amplifier 12 and the ventricular sense amplifier 14 are connected to the heart 16 by way of a suitable lead 18, the constructional features of which are also well known in the art. The outputs from the atrial sense amplifier and the ventricular sense amplifier 14 are applied as inputs to a microprocessor-based controller 20. Associated with the microprocessor-based controller 20 is a crystal controlled clock 22. A bus structure 24 couples the microprocessor-based controller 20 to a ROM memory module 26. The ROM memory is used to store a program of instructions executable by the microprocessor in the microprocessor-based controller 20 for producing control signals for an atrial pace pulse generator 28 and a ventricular pace pulse generator 30. The outputs from these two pulse generators are also applied by way of the lead 18 to appropriate electrodes positioned on or in the heart 16. Also connected to the bus 24 is a random access memory 32 that is used to store operands utilized by the program stored in the ROM memory 26. These operands may include programmed parameters and intermediate computational results developed during execution of the program. In accordance with the present invention, a portion of the RAM memory comprises a buffer 34 that is arranged to store electrogram signals picked up on the lead 18 by the sense amplifiers 12 and 14 and which would include both intrinsic and paced atrial and ventricular depolarization signals. The buffer is of a predetermined length sufficient to store electrogram signals occurring during a predetermined time interval.

Also coupled to the bus 24 is an input/output module 36 which allows two-way communication between the implanted cardiac rhythm management device 10 and an external programmer/monitor 38 by way of a telemetry link 40. It is by way of the monitor 38 and the telemetry link 40 that programmable operands are entered into the RAM memory 32 and information stored in the RAM 32 are transferred to the external monitor for interpretation by a physician or other medical professional.

The implantable cardiac rhythm management device may further include one or more physiologic sensors 42 whereby the pacing rate and other parameters may be made to vary from preprogrammed values to values determined by hemodynamic demand. Such devices are often termed "rate responsive". Although a variety of sensors have been developed for rate adaptive pacing, those detecting activity, acceleration or minute ventilation are perhaps the most common.

Because the clock circuit 22 is crystal controlled, its output is extremely stable in terms of frequency allowing the microprocessor-based controller 20 to maintain a record of the date and time of day.

An important advance that has been made in pacing output circuitry is the concept of automatic capture or autocapture verification and threshold tracking. Capture verification refers to the ability of a pacemaker to detect automatically when a pacing stimulus captures the particular chamber being paced. Threshold tracking uses capture verification as a means to adjust the pacing pulse amplitude automatically to guarantee capture. For example, if capture is verified, the pacing stimulus amplitude remains unchanged. If capture is lost, however, a large-amplitude backup pacing stimulus is delivered (typically within 100 ms) to insure capture of the heart and the amplitude of subsequent pacing stimuli is increased. This basic technique can be modified to track the pacing threshold continuously by algorithmically iterating the output to adjust the stimulus output to a level slightly higher than what is necessary for capture. Paradoxically, continuously adjusting the pacing output to a level that is too close to threshold can actually result in increased energy demand from the battery used to power the implantable device. For each missing beat, the device delivers a large amplitude pacing pulse closely coupled to the ineffective stimulus, and this high-output backup pacing pulse can consume as much as 25 times more energy than a stimulus at threshold. The most common technique used to accomplish autocapture is to measure the evoked response. The evoked response is the alteration of the intracardiac signal in response to the pacing stimulus when capture is achieved. In other words, if capture occurs, an evoked response will arise and can be detected. If capture does not occur, there will be no evoked response.

Figure 2:
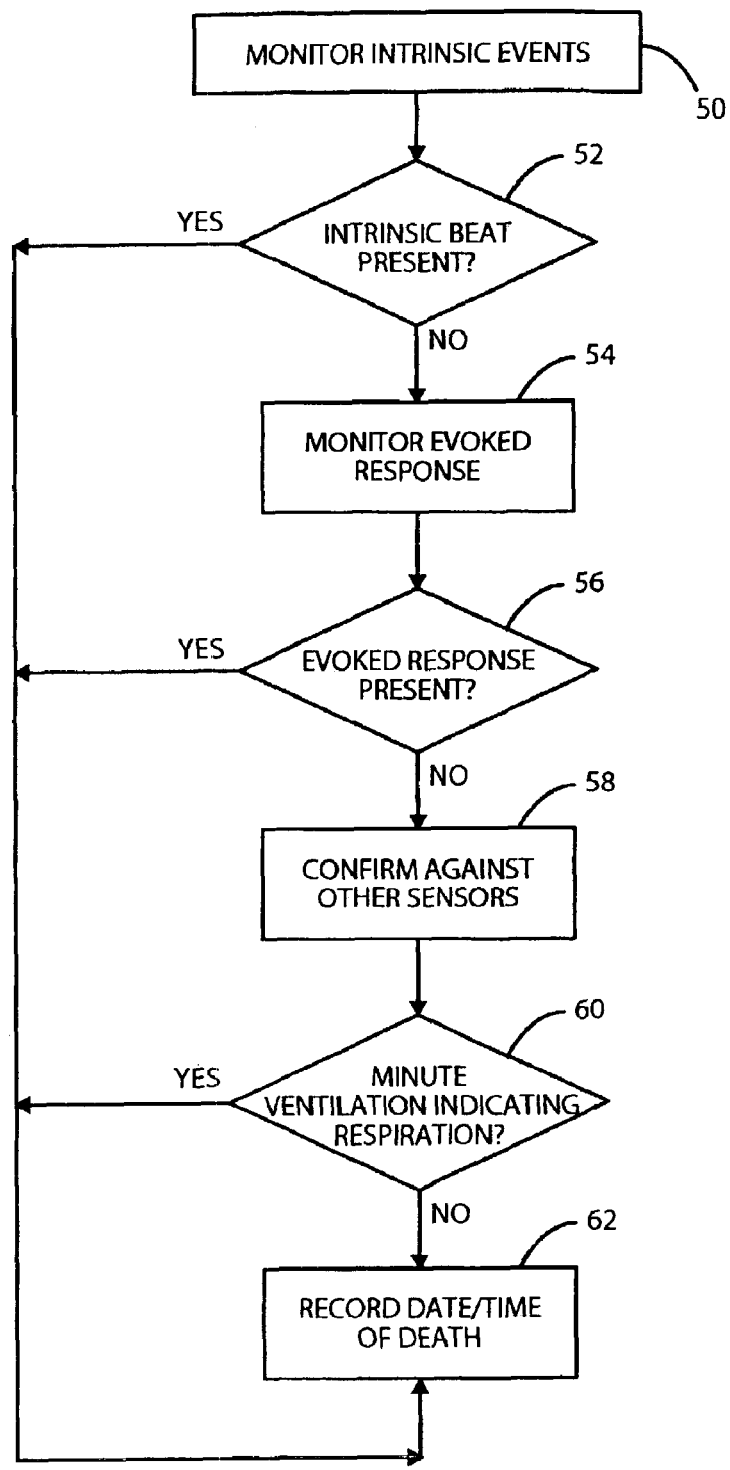
FIG. 2 is a flow diagram illustrating the algorithm of the present invention.
Figure 2:
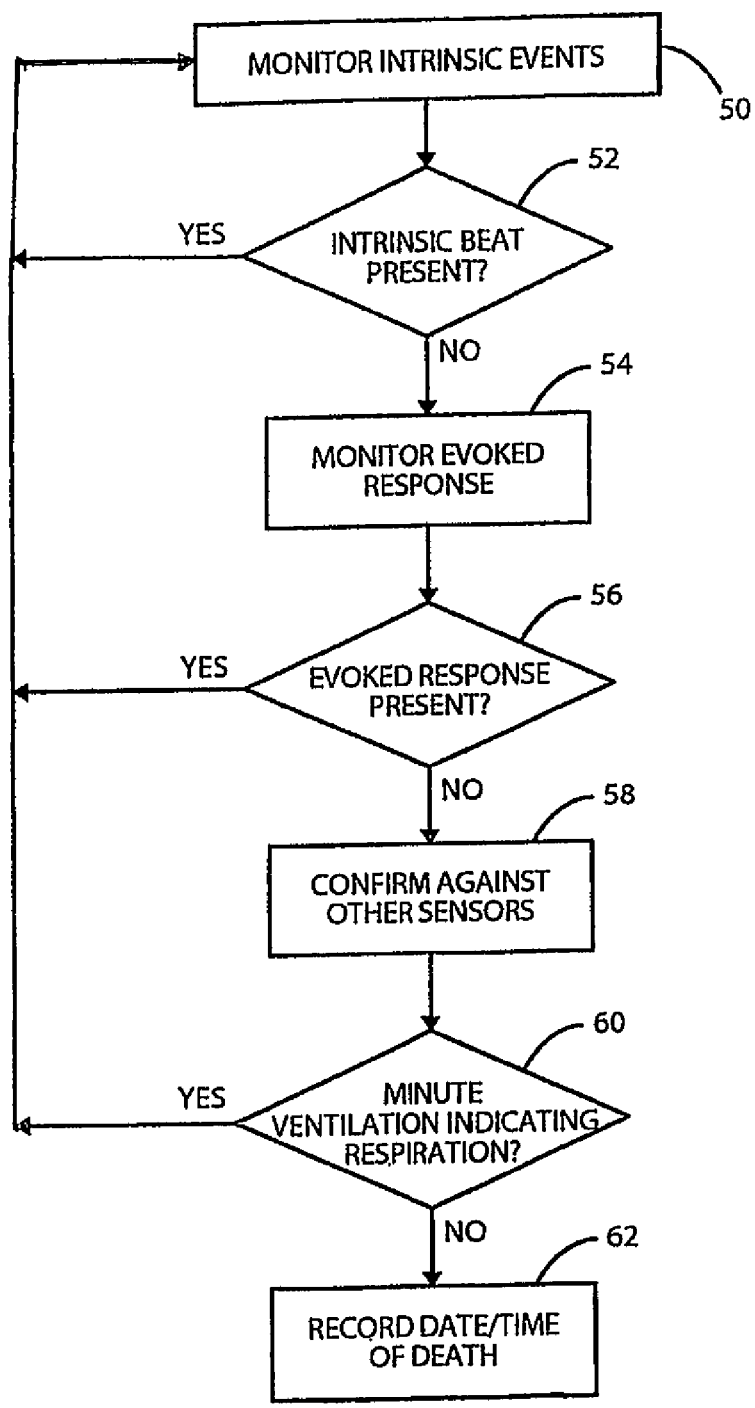
Figure 2:
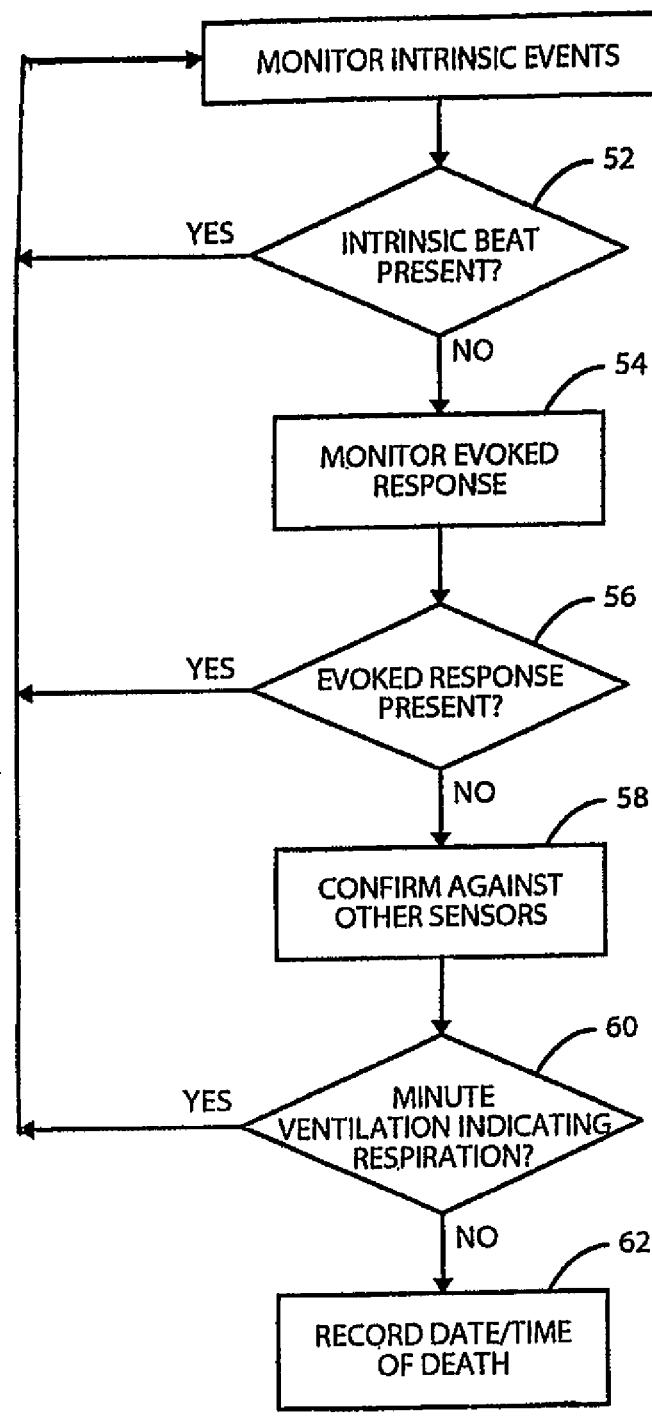

Turning next to FIG. 2 there is set out by means of a software flow diagram the algorithm implemented in the microprocessor-based controller for recording the date and time of cessation of life of a person in whom a pacemaker of the type described is implanted. As represented by box 50, the patient's electrogram is sensed by the sense amplifier 14 to detect the occurrence of intrinsic heartbeats at decision box 52. As long as intrinsic beats are detected, the monitoring operation continues. If an expected intrinsic beat is not detected, the sense amplifiers 12 and 14, or a separate evoked response amplifier (not shown) look for an evoked response resulting from the application of a pace pulse from the pulse generator 30 (box 54). A test is made at decision block 56 to determine whether an evoked response is present. If so, the pacemaker continues to operate in accordance with its control program to produce pacing pulses on a demand basis. However, if no evoked response is present, a check is made of the output of the physiologic sensor 42 which, as mentioned, may comprise an accelerometer, a blood pressure sensor, a minute ventilation sensor or any other physiologic sensor disclosed in the art. See block 58 in FIG. 2. The test made at decision block 60 is to determine whether the sensed physiologic parameter is present. For example, assuming the use of a minute ventilation sensor, the test at decision block 60 is to determine whether the subject is exhibiting respiratory activity. Only if no evoked response to a pacing pulse results and the test at decision block 60 fails to indicate the sensed physiologic response will the date and time of death be stored in the RAM memory 32. See block 62 in FIG. 2. As previously described, sensed electrogram data leading up to the time of death may be captured in the buffer 34 for later read-out to an external monitor 38 via the telemetry link 40 contained within the cardiac rhythm management 10.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

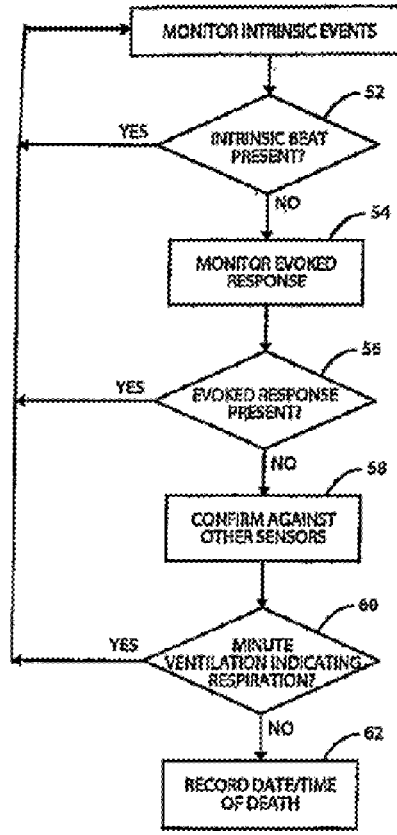

What is claimed is:

1. A method of sensing a death of a patient having an implanted cardiac rhythm management device, said cardiac rhythm management device having a ventricular sensing amplifier for detecting natural and evoked cardiac depolarization signals, a microprocessor-based controller coupled to receive an output from the ventricular sensing amplifier and for developing control signals, and a stimulating pulse generator for producing cardiac stimulating pulses at timed intervals determined by said control signals, comprising the steps of:

(a) monitoring the ventricular sensing amplifier for an evoked response of the patient's heart to the application of the cardiac stimulating pulses; and (b) recording in the cardiac rhythm management device the date and time of death as the date and time at which no intrinsic beat is detected by the ventricular sensing amplifier and application of cardiac stimulating pulses ceases to produce an evoked response.

2. The method as in claim 1 wherein the microprocessor-based controller further includes a buffer memory for storing electrogram signals occurring during a predetermined time interval comprising the further step of capturing the contents of the buffer upon detection that no intrinsic beats are detected and the application of cardiac stimulating pulses to the heart does not result in an evoked response.

3. The method as in claim 1 and further including the step of reading out from the cardiac rhythm management device to an external monitor the date and time of death.

4. The method as in claim 1 wherein the cardiac rhythm management device further includes a physiologic sensor for producing an output signal relating to physiologic events and comprising a further step of monitoring the output signal from the physiologic sensor.

5. The method as in claim 4 wherein the physiologic sensor comprises an accelerometer.

6. The method as in claim 4 wherein the physiologic sensor is a minute ventilation sensor.

7. The method as in claim 4 wherein the microprocessor-based controller includes a buffer memory for storing the output signals of the physiologic sensor and comprising a further step of capturing the contents of the buffer memory upon detection that no intrinsic beats are detected and the application of cardiac stimulating pulses to the heart does not result in an evoked response.

8. The method as in claim 7 and further including the step of reading out from the cardiac rhythm management device the captured contents of the buffer memory to an external monitor.

* * * * *

UNITED STATES PATENT AND TRADEMARK OFFICE
CERTIFICATE OF CORRECTION

PATENT NO.       : 6,904,311 B2
APPLICATION NO.  : 10/326000
DATED            : June 7, 2005
INVENTOR(S)      : Scott Freeberg It is certified that error appears in the above-identified patent and that said Letters Patent is hereby corrected as shown below:

In the Drawings :

Please replace Figure 2 with the attached FIG. 2 as shown on the attached page.

Signed and Sealed this

Fourth Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,904,311 B2 | |
| APPLICATION NO. | : 10/326000 | |
| DATED | : June 7, 2005 | |
| INVENTOR(S) | : Scott Freeberg | |

It is certified that error appears in the above-identified patent and that said Letters Patent is hereby corrected as shown below:

In the Drawings:

Please replace Figure 2 and the print Fig. on the Title Page with the attached FIG. 2 as shown on the attached page.

Signed and Sealed this

Eleventh Day of September, 2007

JON W. DUDAS
*Director of the United States Patent and Trademark Office*

(12) United States Patent
Freeberg

(10) Patent No.: US 6,904,311 B2
(45) Date of Patent: Jun. 7, 2005

(54) METHOD OF DETERMINING AND DOCUMENTING CESSATION OF LIFE USING EVOKED RESPONSE

(75) Inventor: Scott Freeberg, Birchwood Village, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 252 days.

(21) Appl. No.: 10/326,000

(22) Filed: Dec. 19, 2002

(65) Prior Publication Data
US 2004/0122331 A1 Jun. 24, 2004

(51) Int. Cl.$^7$ ............... A61B 5/0402; A61N 1/365; A61N 1/37
(52) U.S. Cl. ............... 600/510; 607/5; 607/9; 607/17; 607/27
(58) Field of Search ............... 600/510, 508–528; 607/17, 27, 4–38

(56) References Cited

U.S. PATENT DOCUMENTS 5,486,200 A * 1/1996 Lindemans .............. 607/5
5,899,866 A * 5/1999 Cyrus et al. ............ 600/510

* cited by examiner

Primary Examiner—Jeffrey R. Jastrzab
Assistant Examiner—Alyssa M Alter
(74) Attorney, Agent, or Firm—Thomas J. Nikolai; Nikolai & Mersereau, P.A.

(57) ABSTRACT

The date and time of death of a patient may be recorded in a memory of a microprocessor used in an implantable cardiac rhythm management device by detecting the failure of the heart to produce an evoked response upon the application of a pace pulse to the heart. To confirm death, other physiologic sensors used in the cardiac rhythm management device may also be sensed to determine the absence of an expected output signal.

8 Claims, 2 Drawing Sheets